United States Patent [19]

Battice et al.

[11] Patent Number: 4,631,297

[45] Date of Patent: Dec. 23, 1986

[54] ANTIMICROBIALLY EFFECTIVE ORGANIC FOAMS AND METHODS FOR THEIR PREPARATION

[75] Inventors: David R. Battice, Midland; Michael G. Hales, Clare, both of Mich.

[73] Assignee: Dow Corning Corporation, Midland, Mich.

[21] Appl. No.: 787,700

[22] Filed: Oct. 15, 1985

Related U.S. Application Data

[63] Continuation of Ser. No. 588,855, Mar. 12, 1984, abandoned.

[51] Int. Cl.⁴ .............................................. C08G 18/14
[52] U.S. Cl. ...................................... 521/78; 55/279; 55/DIG. 13; 210/500.1; 210/502.1; 210/927; 422/122; 521/111
[58] Field of Search ............... 521/78, 111; 210/500.1, 210/502.1, 927; 55/279, DIG. 13; 422/122

[56] References Cited

U.S. PATENT DOCUMENTS

| | | | |
|---|---|---|---|
| 3,511,788 | 5/1970 | Kelh | 528/28 |
| 3,661,963 | 5/1972 | Pape et al. | 528/28 |
| 3,730,701 | 5/1973 | Isquith et al. | 528/28 |
| 3,794,736 | 2/1974 | Abbott et al. | 528/28 |
| 3,817,739 | 6/1974 | Abbott et al. | 528/28 |
| 3,865,728 | 2/1975 | Abbott et al. | 528/28 |
| 4,059,581 | 11/1977 | Prokai | 521/111 |
| 4,259,103 | 3/1981 | Abbott et al. | 528/28 |
| 4,282,366 | 8/1981 | Eudy | 528/28 |
| 4,394,378 | 7/1983 | Klein | 528/28 |
| 4,406,892 | 9/1983 | Abbott et al. | 528/28 |

FOREIGN PATENT DOCUMENTS

1010782 of 0000 Canada .
55-133449 10/1980 Japan .
57-59927 4/1982 Japan .

OTHER PUBLICATIONS

Procedures of the Society of Plastic Ind., 27th Annual Tech/Mkt. Mtg. of the Unithane Division Oct. 20-22, 1982 Bal Harbour, Fla. p. 308.
Modern Floor Coverings, Suppliers Slants p. 37, Aug. 1983.
Isquith, Abbott, Walters, Applied Microbiology, 1972, pp. 859-863.
Walters, Abbott and Isquith, Applied Microbiology, 25, No. 2, pp. 253-256, Feb. 1973.

*Primary Examiner*—Maurice J. Welsh
*Attorney, Agent, or Firm*—Robert L. McKellar

[57] ABSTRACT

What is disclosed is a method for preparing antimicrobially effective foams using certain silanes as co-catalysts, co-surfactants and antimicrobial agents to give soft, resilient, fine-celled foams that are capable of reducing the number of, or eliminating, microorganisms in all types of media. Such foams themselves are not susceptible to attack by the microorganisms. An example is the use of $(CH_3O)_3Si(CH_2)_3N^{\oplus}(CH_3)_2C_{18}H_{37}Cl^-$ in a flexible polyurethane foam formulation to give a fine-celled, soft, resilient foam which is antimicrobially effective over a long period of time.

108 Claims, No Drawings

ANTIMICROBIALLY EFFECTIVE ORGANIC FOAMS AND METHODS FOR THEIR PREPARATION

This is a continuation of co-pending application Ser. No. 588,855 filed on Mar. 12, 1984, now abandoned.

BACKGROUND OF THE INVENTION

Organic polymers have a large number of different chemical structures which cause them to range from solids to high viscosity liquids. These materials resemble each other in their behavior owing to the fact that they are almost always high molecular weight materials which ultimately provide their cured forms the necessary physical properties to allow them to be used in a general category known as plastics which includes almost every known polymer. These polymers are molded, formed, cast, extruded, foamed and otherwise handled in order to obtain millions of products used worldwide.

One category of plastics handling that has rapidly evolved since the 1950's is the foamed product, most notably polystyrene, polyvinylchloride, and polyurethane foams, even though other polymers can also be foamed, such as nylon, polyethylene, polypropylene, polyterephthalates, polyvinyl, alkyl ethers, polyvinylidine chloride, polyvinylidinefluoride and some of the lesser known materials such as polyxylenenes and polysulfones.

Cellular products resulting from the foaming of the above polymers are subject to microbial attack, either because the polymer itself is a food source for such microorganisms or because the reticulated form of the polymer allows the collection of debris which serves as a food source for the microorganisms.

It would be beneficial if the reticulated products themselves could be used in applications wherein preservation of some other medium is desired, for example, pasteurization of milk and milk products. Also, it would be beneficial if the reticulated products could be substituted in other applications where it is desirable to reduce the number of microorganisms in a medium, such as, for example, air or water as disclosed in U.S. Pat. No. 3,730,701, issued May 1, 1973; U.S. Pat. No. 3,817,739, issued June 18, 1974 and U.S. Pat. No. 3,865,728, issued Feb. 11, 1975.

Such similar uses have been anticipated and there are products being sold for domestic use which are foamed products that contain antimicrobial agents. For example, 10,10'-oxybisphenoxarsine (OBPA) has been used in polyurethane foam as an antimicrobially effective carpet underlay. See "Manifestations of Microbiological Growth on Urethane Foam", Proceedings of the Society of Plastics Industries 27th Annual Tech/Mkt. Meeting of the Urethane Division, Oct. 20–22, 1982, Bal Harbour, Florida, page 308, and Modern Floor Coverings, Supplier Slants, "GFC Ranks High In Service, Innovation", page 37, August 1983.

There are certain problems, however, with these types of antimicrobial agents in polyurethane foams. For example, such agents leach from the foams. Further, the leachate-agent, once free from the underlay can move into the carpet itself whereby it can be contacted by humans and pets. Because of the leaching, the antimicrobial effect of the carpet underlay is not durable. Further, it has been demonstrated that such agents, especially OBPA, are adapted-to by the microorganism over a period of time so that the agent is ineffective against future generations of the organisms.

Thus, it is an objective of the instant invention to provide new and improved foamed polymers that will overcome the prior art problems.

THE INVENTION

The instant invention deals with a method of preparation of antimicrobially effective organic foams; the antimicrobial effective foams themselves and their end uses. More specifically, it is an objective of this invention to prepare antimicrobially effective foams from all types of organic polymers that are foamable, either chemically, mechanically or gas or air blown.

It is also an objective of this invention to prepare antimicrobially effective foams whose effectiveness is enhanced.

It is another objective of this invention to prepare foams whose antimicrobial effectiveness is durable.

It is still another objective of this invention to prepare foams whose antimicrobial effectiveness is broad spectrum.

It is yet another objective of this invention to prepare foams containing antimicrobial agents that are non-adaptive to common microorganisms.

It is a further objective of this invention to prepare certain antimicrobially effective foams that have fine, uniform cell structure, controlled variable densities, improved foam resiliency and softness.

It is still further an objective of this invention to prepare antimicrobially effective foams in a process whereby toxic ingredients, commonly used in the preparation of the foams, can be eliminated or drastically reduced.

Finally, it is an objective of this invention to manufacture antimicrobially effective foams that can be used in applications heretofore not using antimicrobial foams, and it is an objective of this invention to replace commercially manufactured foams, currently used in certain applications requiring antimicrobial effectiveness, that use leachable, non-durable antimicrobial agents.

It could not have been anticipated that the silanes of the instant invention could also function as foam-specific surfactants in a foamed system while also lending durable antimicrobial effects to the resulting foam.

These and other objectives can be achieved by the use of the instant invention which consists of a process for preparing an antimicrobially effective stable foam which comprises (I) contacting, and intimately mixing, prior to foaming, a foamable organic system and an organosilane having the general formula selected from the group consisting of

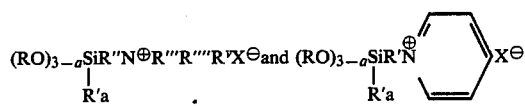

wherein, in each formula, R is an alkyl radical of 1 to 4 carbon atoms or hydrogen; a has a value of 0, 1 or 2; R' is a methyl or ethyl radical; R" is an alkylene group of 1 to 4 carbon atoms; R''', R'''', and R$^v$ are each independently selected from a group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$, wherein x has a value of from 2 to 10 and R$^{vi}$ is a perfluoroalkyl radical having from 1 to 12 carbon atoms; X is chloride, bromide, fluoride, iodide, acetate or tosylate; (II) foaming the mixture from (I), and (III) allowing the foamable organic system to stabilize, whereby an antimicrobially active stable foam is obtained.

This invention further deals with the foam products produced by such a process and the use of the foam products for many applications requiring an antimicrobially effective foam.

The process of this invention consists of adding one of the above described silanes to a foamable system prior to the time that the foam is stabilized and preferably before the foamable system is foamed. By "stabilized", it is meant for purposes of this invention that the foam material is not readily capable of reverting to its precursors. This includes chemically reacted cured foams as well as "air-dried" foams, and plastisols which are plasticized, high molecular weight polymers such as polyvinylchloride. Stabilization for purposes of this invention means heat cured; catalyzed, heat cured; cooling; or simple solvent evaporation, just as long as the foamed products are incapable, after such treatment, of easily reverting to the precursor state. An example of heat and catalyst cure is polyurethane foam; an example of air-dried foam is latex rubber foam and polyvinyl chloride plastisols, and an example of heat cured foam is polystyrene foam.

For purposes of this invention, any method by which the silane and the foamable organic system can be intimately mixed is useable herein. The silanes are heat stable to a great degree, and therefore any method of mixing which requires that the organic polymer system be in the molten state, to achieve intimate mixing of the silane and the organic polymer system, is included within the scope of this invention. The object of the intimate mixing is to give a uniform dispersment of the silane in the organic polymer system. Also, the silanes useful in this invention are essentially shear resistant, and therefore, any method of intimately mixing the silane and the organic polymer system by mechanical means is useful in this invention.

As soon as the silane and the organic polymer system are intimately mixed, steps are taken to foam the system and stabilize the foam. In some cases, it is obvious that the intimate mixing method also creates the foam. In other cases, such as, for example, polyurethane foams, even though the intimate mixing froths the mixture, the final foam is obtained by allowing the ensuing chemical reaction, with the resultant evolution of carbon dioxide to create the foam. In the first case, heat, for example, may have to be used to set and stabilize the foam, while in the latter case, the foam is allowed to rise and set and then the foam is further cured by the application of heat to stabilize the foam.

From a compatibility standpoint, there appears to be no limitations on the amount of silane that can be used, especially, if the foamable organic system is heterogeneous.

For purposes of this invention, there is used about 0.25 to 14 parts of silane per 100 parts of foamable organic system. This equates to about 0.1 to 6 parts/100 parts of polyol in a polyol-based system. Most preferred, however, is about 0.5 to 5 parts of silane per 100 parts of foamable organic system. For example, in a flexible polyurethane foam system, it is desirable to use about 0.5 to 3.25 parts of silane per 100 parts of foamable organic system which is about 0.75 to 5 parts per 100 parts of polyol used in the foamable system.

Once the foam is stabilized, it can be shaped and cut to provide the products of this invention. It is also contemplated in this invention that the foamed products can also be molded or foamed during molding to achieve certain parts.

The silanes useful in this invention have the general formula

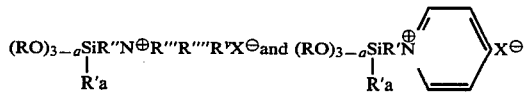

It should be noted that generically, these materials are quaternary ammonium salts of silanes. Most of the silanes falling within the scope of this invention are known silanes and references disclosing such silanes are numerous. One such reference, U.S. Pat. No. 4,259,103, issued to James R. Malek and John L. Speier, on Mar. 31, 1981, discusses the use of such silanes to render the surfaces of certain substrates antimicrobial. Canadian Pat. No. 1,010,782, issued to Charles A. Roth shows the use of fillers treated with certain silanes to be used in paints and the life to give antimicrobial effects.

Numerous other publications have disclosed such silanes, namely, A. J. Isquith, E. A. Abbott and P. A. Walters, Applied Microbiology, December, 1972, pages 859–863; P. A. Walters, E. A. Abbott and A. J. Isquith, Applied Microbiology, 25, No. 2, p. 253–256, February 1973 and E. A. Abbott and A. J. Isquith, U.S. Pat. No. 3,794,736 issued Feb. 26, 1974, U.S. Pat. No. 4,406,892, issued Sept. 27, 1983, among others.

For purposes of this invention, the silanes can be used neat or they can be used in solvent or aqueous-solvent solutions. When the silanes are used neat, the inventive process is preferably carried out in a system in which some small amount of water is present. For example, polyurethane foam systems are very good for this type of application because the formulations inherently contain water. Further, if it is not possible to have a system with some small amount of water present, then a water soluble or water-dispersable, low molecular weight hydrolyzate of the silane may be used. What is important is the fact that the durability of any effect produced by the silane as part of a foamed product requires that the silane molecule react with the foamable organic polymer system to a certain extent. The most reactive species, as far as the silanes are concerned, is the $\equiv$SiOH that is formed by hydrolysis of the alkoxy groups present on the silane. The $\equiv$SiOH groups tend to react with the foamable organic polymers and bind the silanes to the resulting foam. It is believed by the inventors even though the prime mode of coupling to the foamable organic system is by the route described above, it is also believed by the inventors that the alkoxy groups on the silicon atom may also participate in their own right to bind to the foamable polymer.

Preferred for this invention is a reactive foamable organic polymer system containing some small amount of water. By "reactive", it is meant that the polymers system must contain some groups which will react with some of the silanols generated by hydrolysis of the silanes of this invention.

R in the silanes of this invention are alkyl groups of 1 to 4 carbon atoms. Thus, useful as R in this invention are the methyl, ethyl, propyl and butyl radicals. R can also be hydrogen thus indicating the silanol form, i.e. the hydrolyzate. The value of a is 0, 1 or 2 and R' is a methyl or ethyl radical.

R" for purposes of this invention is an alkylene group of 1 to 4 carbon atoms. Thus, R" can be alkylene groups such as methylene, ethylene, propylene, and butylene. R''', R'''', and $R^v$ are each independently selected from a group which consists of alkyl radicals of 1 to 18 carbons, $-CH_2C_6H_5$, $-CH_2CH_2OH$, $-CH_2OH$, and $-(CH_2)_xNHC(O)R^{vi}$. x has a value of from 2 to 10 and $R^{vi}$ is a perfluoroalkyl radical having from 1 to 12 carbon atoms. X is chloride, bromide, fluoride, iodide, acetate or tosylate.

Preferred for this invention are the silanes of the general formula

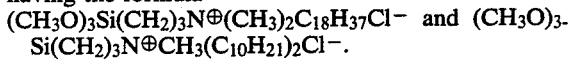

wherein R is methyl or ethyl; a has a value of zero; R" is propylene; R''' is methyl or ethyl; R'''' and $R^v$ are selected from alkyl groups containing 1 to 18 carbon atoms wherein at least one such group is larger than eight carbon atoms and x is either chloride, acetate or tosylate.

Most preferred for this invention are those silanes having the formula
$(CH_3O)_3Si(CH_2)_3N^{\oplus}(CH_3)_2C_{18}H_{37}Cl^-$ and $(CH_3O)_3Si(CH_2)_3N^{\oplus}CH_3(C_{10}H_{21})_2Cl^-$.

As indicated above, most of these silanes are known from the literature and methods for their preparation are known as well. See, for example, U.S. Pat. No. 4,282,366, issued Aug. 4, 1981; U.S. Pat. No. 4,394,378, issued July 19, 1983, and U.S. Pat. No. 3,661,963 issued May 9, 1972, among others.

The foamable organic systems preferred in this invention include polyurethane, polystyrene, nylon, polyethylene, polypropylene, polyterephthalates, polyvinylalkylethers, polyvinylchloride and polyvinylidene chloride and fluoride which are reactable with the silanes of this invention in the presence of water.

Preferred for this invention are polyurethanes, polystyrene, polyethylene and polyvinylchloride.

Most preferred are the polyurethane foams and contemplated within the scope of this invention are flexible, semi-flexible, and rigid, as well as high resiliency foams. Both polyether based and polyester based foams are included herein.

All of these types of foams and the methods for their preparation are well known in the art and therefor such preparations will not be detailed herein.

When the silanes of this invention are utilized in chemically reactive foams systems such as the polyurethanes, there are several advantages that are obtained. The silanes lend a catalytic effect as well as a surfactant effect to the foam during preparation. For example, the foams obtained by the use of the silanes are fine-celled, uniform foams. Variable densities of foam can be obtained using these silanes. Further, one can use less tin salts in the foam formulation which allows the foam to be less toxic as a result. Also, less amine catalyst can be used. The foams are resilient and are very soft.

The foams of this invention inhibit the growth of bacteria; have a durable antimicrobial effect; are highly antimicrobially effective; are non-adaptive to microorganisms and have broad spectrum activity toward common microorganisms.

Thus, these foams are useful in such applications as backings for carpets, curtains, wall rugs and wall hangings; mattresses, cushions, such as automobile cushions, furniture cushions, pillows, lapidus pads, decubitus pads, air filters such as, clean room air filters, air conditioner filters, industrial and automotive filters; filters for liquids such as blood, blood products and fermented spirits, such as, for example, beer and wine; water filters for pools, coolant systems, waste water, non-potable water, aquarium filters; milk filtration and pasteurization; sponges; humidifier belts and pads; thermal insulation, for example, in walk in coolers; gas filters such as, for example, oxygen, nitrogen and carbon dioxide and many other uses where the reduction in number or elimination of microorganisms is desired.

The following glossary identifies the reagents used in the examples and the manufacturer, if known.

GLOSSARY

Toluene diisocyanate—This material as used herein consisted of an 80/20 weight percent mixture of 2,4-toluene diisocyanate and 2,6-toluene diisocyanate.

Voranol ® CP-3810—This material is a water insoluble polyether triol of alkyleneoxide containing 10 weight % ethylene oxide and 90 weight % propyleneoxide and it has an average molecular weight of 3800. It is manufactured by the Dow Chemical Company, Midland, Mich., USA and Voranol ® is a registered trademark of that company.

Voranol ® 4701—This material is a 4700 molecular weight polyether polyol for the preparation of high resiliency, flexible polyurethane foam. It has a hydroxyl number of 34 and a viscosity @ 25° C. of 865 cs. It is manufactured by the Dow Chemical Company, Midland, Mich., USA.

Polycat ® 8—This material is a tertiary amine catalyst for use in preparation of rigid urethane foam. It is manufactured by Abbott Laboratories, North Chicago, Ill., USA. Polycat is a registered trademark of that company.

Fyrol ® 6—This material is a chlorinated phosphate ester used as a fire retardant in rigid urethane foam. It is manufactured by Stauffer Chemical Company, Westport, Conn., USA. Fyrol is a registered trademark of that company.

DC ® 1250 Surfactant—This material is a resinous silicone co-polymer used to stabilize frothed vinyl foam. DC ® 1250 has a viscosity at 25° C. of 6 cs; specific gravity at 25° C. of 1.00 and is described in U.S. Pat. No. 3,511,788. It is manufactured by Dow Corning Corporation, Midland, Mich., USA.

Pluracol ® 684—P-684 is an acrylonitrile-styrene containing graft polyol for preparation of very high load bearing flexible slab stock foam.
Hydroxyl #36
Viscosity cps @ 25° C.—3000
Appearance—opaque, pale yellow liquid
This material is manufactured by B.A.S.F. Wyandotte Corporation, Wyandotte, Mich., USA. Pluracol is a registered trademark of that company.

Pluracol ® 364—P-364 is a sucrose based polyether polyol for preparation of low density rigid urethane foam. It is manufactured by B.A.S.F. Wyandotte Corporation, Wyandotte, Mich., USA.

Niax ® 34-28 Polyol—This material is a reactive primary hydroxyl polymer polyol for preparation of high resiliency urethane foam.
Hydroxyl #28
Viscosity cps @ 25° C.—1958 m.w.-5000

It is manufactured by Union Carbide Corporation, New York, N.Y., USA. Niax is a registered trademark of that company.

Niax ® A-1—This material is an amine catalyst for polyurethane foam systems. It is manufactured by the Union Carbide Corporation, Charleston, W. Va., USA. Niax ® is a registered trademark of this company.

Niax ® ES—This material is a silicone-amine catalyst used for polyester foam systems. It is manufactured by the Union Carbide Corporation, New York, N.Y., USA.

Niax ® L-536—This material is a non-hydrolyzable silicone glycol co-polymer for stabilizing polyester flexible urethane foam. This surfactant is manufactured by the Union Carbide Corporation, New York, N.Y., USA.

Niax ® Blowing Agent 11—This material is an uninhibited fluorocarbon for use where stability is unnecessary. It is most commonly used as an auxiliary blowing agent in flexible urethane foam. It is manufactured by the Union Carbide Corporation, New York, N.Y., USA.

Niax ® Blowing Agent 11B—This material is an inhibited fluorocarbon used as an auxiliary blowing agent in urethane foam premixes where long term stability is required. It is manufactured by the Union Carbide Corporation, New York, N.Y., USA.

Niax ® E.S. Catalyst—This material is a silicone/amine catalyst used for polyester foam systems. It is manufactured by the Union Carbide Corporation, New York, N.Y., USA.

Voranol ® 4701 Polyol—This material is a 4700 m.w. polyether polyol for the preparation of high resiliency flexible polyurethane foam.
Hydroxyl #—~34.0
Viscosity ≈250° C.—865 cps
It is manufactured by the Dow Chemical Company, Midland, Mich., USA.

Foamrez ® 50—This material is a 2000 m.w. diol, polyester resin for preparation of flexible polyester urethane foam.
Hydroxyl #—55
Viscosity @25° C.—20,000 cps
It is manufactured by Witco Chemical Company, Perth Amboy, N.J. USA. Foamrez is a registered trademark of that company.

Baircat ® B-16—This material is a hexadecyl dimethylamine

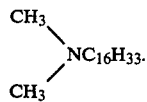

It is an amine catalyst used in preparation of flexible polyester urethane foam. It is manufactured by Lonza Inc., Fairlawn, N.J. USA. Baircat is a registered trademark of that company.

Thermolin ® 101—This material is tetrakis(2-chloroethyl)ethylene diphosphate, $C_{10}H_{20}Cl_4O_8P_2$ (chlorinated phosphate ester), used as a fire retardant in urethane foam. It is manufactured by Olin Chemical Corporation, Stanford, Conn., USA. Thermolin is a registered trademark of that company.

Dabco ® 33LV—This material is a tertiary-amine catalyst for use in urethane foam.

33.3% Dabco (triethylenediamine)
67.7% dipropylene glycol
It is manufactured by Air Products Company, Paulsboro, N.J., USA. Dabco is a registered trademark of that company.

Witco UL1 Tin Catalyst—This material is a tin catalyst used in polyurethane foam formulations. It is manufactured by Witco Chemical Company, Perth Amboy, N.J., USA.

Bordon ® 411 Homopolymer—This material is a polyvinylchloride resin manufactured by the Borden Chemical Company, Leominster, Mass., USA.

Dowanol ® EM—This material is $CH_3OCH_2CH_2OH$. It is manufactured by the Dow Chemical Company, Midland, Mich., USA. Dowanol is a registered trademark of that company.

Arquad ® T27W—This material is a mixture of $(CH_3)_3N^+C_{16}H_{33}Cl^-$ and $(CH_3)_3N^+C_{18}H_{37}CL^-$ @100% solids. It is manufactured by Armak Company, Chicago, Ill., USA. Arquad is a registered trademark of that company.

Zephiran ®—This material is $C_{12,14,16}N^+(CH_3)_2Cl^-$. It is manufactured by Winthrop Laboratories, New York, N.Y., USA. Zephiran is a registered trademark of that company.

Triton ® X-100—This material is $C_8H_{17}C_6H_4(OCH_2CH_2)_9OH$. It is manufactured by Rohm and Haas, Philadelphia, Pa., USA. Triton is a registered trademark of that company.

T-10—This material is a tin catalyst used in polyurethane foam formulations, i.e. stannous octoate in which 50% of the octoate groups have been substituted with dioctylphthalate groups. It is manufactured by M and T Chemicals, Rahway, N.J., USA.

Mondur ® M.R.—This material is a polymethylene polyphenyl isocyanate.
NCO %=31.5; amine equivalent 133;
Viscosity @25° C. is 200 Pa·s;
Density g/cc is 1.24
It is manufactured by Mobay Chemical Company, Pittsburg, Pa., USA. Mondur is a registered trademark of that company.

The following examples illustrate the invention but are not to be construed as limiting the invention as defined and set forth in the claims.

Standard Procedure "A"—Standard Polyurethane Foam Procedure:

Standard polyether-based polyurethane foam was prepared for purposes of this invention by preparing a component "A" and a component "B" in the following manner: Component A was toluene diisocyanate with an isocyanate index of 105. Component "B" was a mixture of the following:

| Parts by Weight | Ingredient |
|---|---|
| 100 | Voranol ® CP3810 |
| 4.5 | Water deionized |
| 0.09 | Niax ® A-1 |
| 0.8 | silicone surfactant (a siloxane-polyoxyalkylene copolymer surfactant manufactured by the Dow Corning Corporation, containing 31.4% ethylene oxide units and 35.8% propylene oxide units; specific gravity of 1.03 @25° C.; viscosity of 1000 cps; density of 8.59 lbs/gal. @25° C., used for flexible foam) |
| 0.4 | T-10 |
| 3.25 | methylene chloride |

Generally, the usual method is to combine the ingredients of component "B" in any suitable container, usually in a 1 quart paper cup, and homogenize them using any suitable means such as an Eppenbach Mixer or the like. Component "A" is then added, the mixture again homogenized and the foam allowed to rise in the container. The foam is then stabilized at elevated temperatures, usually 200° F. and then removed from the 1 quart container.

The antimicrobial agents are generally added at a rate based on 100 parts of the polyol.

Whenever the foams are described as "acceptable", it means they have the normal appearance and physical properties of standard polyurethane foam. Further, foam height in this specification is described in two numbers as inches and sixteenths of inches, for example 9-8 means nine and eight-sixteenths inches in height.

Air flow is the term used by the urethane foam industry to measure the relative porosity of flexible urethane. It is usually reported in ft.$^3$/min. of air that can be passed through the foam sample. 1.0-3.0 ft.$^3$/min. is typically considered low air flow. 3.0-6.0 ft.$^3$/min. is considered medium air flow. 6.0-10.0 ft.$^3$/min. is considered high air flow.

Standard Test "B"—Determination of Substantivity of the Antimicrobial Agent on Foam.

The anion of an aqueous sodium salt of bromphenol blue can be complexed with the cation of a polymerized silane of this invention while it is on a substrate. The blue colored complex, substantive to a water rinse, is qualitatively indicative of the presence of the cation on the substrate thus indicating the extent of antimicrobial agent on a given substrate. A comparison of the intensity of retained blue color to a color standard is used as a check to determine if the treatment has been applied properly.

The method consists of preparing a 0.02 to 0.04 weight percent solution of bromphenol blue in distilled water. This solution is made alkaline using a few drops of saturated $Na_2CO_3$ solution per 100 milliliters of the solution. Two to three drops of this solution are placed on the treated substrate and allowed to stand for two minutes. The substrate is then rinsed with copious amounts of tap water and the substrate is observed for a blue stain and it is compared to a color standard.

For a spectrophotometric determination, the following test is used.

The sodium salt of bromphenol blue is depleted from a standard solution by complexing with the cations on a treated substrate. The change in bromphenol blue concentration is determined spectrophotometrically or by comparison with color standards whereby the level of substrate treatment by the cationic silane is determinable.

The method consists of preparing a 0.02 weight percent standard solution of bromphenol blue in distilled water. It is made alkaline with a few drops of saturated $Na_2CO_3$ solution per 100 milliliters of bromphenol blue solution. The color of this solution is purple.

The blank solution is adjusted to yield a 10 to 12% transmittance reading when measured in 1 cm cells using a spectrophotometer set at 589 nm by the following method.

Fill a container ¾ full of distilled water and add 2 ml of the 0.02% standard bromphenol blue solution for every 50 ml of distilled water. Add 0.5 ml of a 1% Triton ® X-100 surfactant (manufactured by Rohm and Haas, Philadelphia, PA, USA) aqueous solution for every 50 ml of water. Mix, and using the spectrophotometer, determined the maximum absorbance. Adjust the upper zero to 100% transmittance with distilled water. Check the percent transmittance of the working bromphenol blue solution at the maximum absorbance setting. Adjust the blank solution to 10 to 12% transmittance with either water or bromphenol blue standard solution as necessary.

The samples of treated substrate are tested by placing 0.5 gram samples of the substrate standards in a flask large enough for substantial agitation of the sample and the test solution. Add 50 ml of the working solution. Agitate for 20 minutes on a wrist-action shaker. Fill the test curvette with the test solution. Centrifuge if particulate matter is present. Measure the % transmittance at the wavelength set forth above. The transmittance is compared against a standard curve prepared by preparing several substrate samples of known concentration of the cationic silane. For example, samples containing a known amount of cationic silane at, for example, 0%, 0.25%, 0.50%, 0.75% and 1% are read spectrophotometrically and a curve is plotted.

Standard Test "C"—Antimicrobial Activity by Dynamic Test of Surfaces

The antimicrobial activity of a treated surface is evaluated by shaking a sample weighing 0.75 grams in a 750,000 to 1,500,000 count *Klebsiella pneumoniae* suspension for a one hour contact time. The suspension is serially diluted, both before and after contact, and cultured. The number of viable organisms in the suspensions is determined. The percent reduction based on the original count is determined. The method is intended for those surfaces having a reduction capability of 75 to 100% for the specified contact time. The results are reported as the percent reduction.

Media used in this test are nutrient broth, catalog No. 0003-01-6 and tryptone glucose extract agar, catalog No. 0002-01-7 both available from Difco Laboratories, Detroit, Mich., U.S.A. The microorganism used is *Klebsiella pneumoniae* American Type Culture Collection; Rockville, Md. U.S.A., catalong No. 4352.

The procedure used for determining the zero contact time counts is carried out by utilizing two sterile 250 ml. screw-cap Erlenmeyer flasks for each sample. To each flask is added 70 ml of sterile buffer solution. To each flask is added, aseptically, 5 ml of the organism inoculum. The flasks are capped and placed on a wrist action shaker. They are shaken at maximum speed for 1 minute. Each flask is considered to be at zero contact time and is immediately subsampled by transferring 1 ml of each solution to a separate test tube containing 9 ml of sterile buffer. The tubes are agitated with a vortex mixer and then 1 ml of each solution is transferred to a second test tube containing 9 ml of sterile buffer. Then, after agitation of the tubes, 1 ml of each tube is transferred to a separate sterile petri dish. Duplicates are also prepared. Sixteen ml of molten (42° C.) tryptone glucose extract agar is added to each dish. The dishes are each rotated ten times clockwise and ten times counterclockwise. The dishes are then incubated at 37° C. for 24 to 36 hours. The colonies are counted considering only those between 30 and 300 count as significant. Duplicate samples are averaged. The procedure used for determining the bacterial count after 1 hour is essentially the same as that used to determine the count at the zero contact time. The only difference is that pour plating is performed at the $10^0$ and $10^{-1}$ dilutions as well as at the $10^{-2}$ dilution. "Percent reduction" is calculated by the formula $$\%R = \frac{\frac{B+C}{2} - A}{\frac{B+C}{2}} 100$$

where A is the count per milliliter for the flask containing the treated substrate; B is zero contact time count per milliliter for the flask used to determine "A" before the addition of the treated substrate and C is zero contact time count per milliliter for the untreated control substrate.

EXAMPLE 1

Standard Flexible Polyether-based Polyurethane Foam

A flexible polyurethane foam was prepared in a paper cup in the following manner: the system consisted of part A which was toluene diisocyanate (105 index) and part B was a mixture as follows:

| Parts by weight | Ingredient |
|---|---|
| 100 | Voranol ® CP-3810 polyol |
| 4.5 | deionized water |
| 0.09 | Niax ® A-1 |
| 0.8 | Silicone surfactant (as used in Standard Procedure "A") |
| 0.4 | T-10 catalyst |
| 3.25 | $CH_2Cl_2$ |

There was added to this basic formulation in parts by weight based on 100 parts of polyol, an organosilane of this invention as shown on Table I below and then part A was added at 53 parts by weight and the entire mixture stirred according to the above described standard procedure "A". Immediately after stirring, the foaming mixture was transferred by pouring to a clean paper cup and it was allowed to foam and rise. The cup of foam, when it had finished foaming, was placed in a 200° F. over for 15 minutes to stabilize the foam. The organosilane in this example was $(CH_3O)_3Si(CH_2)_3N^+(CH_3)_2C_{18}H_{37}Cl^-$. % transmittance was derived by applying standard test "B" to the foam samples. % reduction was derived by applying standard test "C" to foam samples. The results can be found in Table I below.

TABLE I

| | Results of Example 1 | | |
|---|---|---|---|
| Sample | Organosilane pbw/100 pbw of polyol | % transmittance | % reduction |
| A | 1 | 24.5 | 94.0 |
| B | 3 | 97.1 | 100 |
| C | 5 | 99.2 | 100 |
| Control | 0 | 12.8 | 0 |
| Blank* | — | 10.5 | — |

*See Standard Test "B"

It will be recalled that standard test "B" depends on the complexing of the quaternary silane with bromphenol blue in solution. During this test on the above samples, almost all of the bromphenol blue was exhausted from the solution onto the foam substrate when the two samples B and C were tested. Normally, when a substrate is merely treated with the organosilane, such as dabbing, soaking or spraying, at a level of 1 weight percent or greater, some of the chemical (excess) during this test washes off the substrate, or the substrate abrades carrying with it the organosilane, which complexes with the bromphenol blue in solution yielding a blue solution rather than a purple solution that is normally expected. The samples B and C therefore, must have co-reacted the organosilane to the urethane foam thus making the organosilane unavailable to complex with the bromphenol blue. It appears therefore that the foamed product containing the organosilane binds the organosilane and renders the foam permanently antimicrobial without any leaching of the organosilane from the substrate. Thus, the foam itself is antimicrobial rather than being a foam which has been treated to render it antimicrobially effective. It should be noted, that for this type of foam, the foam was capable of 100% reduction of the microbes in the test media for the levels of 3 to 5 parts by weight while even at the one part level, the foam reduced the microbes by 94%. These foams were fine-celled and soft and of essentially the same height and weight as the control foam.

EXAMPLE 2

Carpet Underlay Foam

The organosilane $(CH_3O)_3Si(CH_2)_3N^+(CH_3)_2C_{18}H_{37}Cl^-$ was found to be highly compatible with and capable of producing a carpet underlay foam. It is prepared in the following manner: the system consisted of part A which was toluene diisocyanate (105 index) and part B was a mixture as follows:

| Ingredient | Parts by weight |
|---|---|
| Pluracol ® polyol 684 | 100 |
| deionized water | 3.0 |
| Surfactant (same as used in Standard Procedure "A") | 1.0 |
| Dabco ® 33LV | 0.25 |
| Thermolin ® 101 | 2.0 |

This mixture also contained barium sulfate and calcium carbonate as fillers.

The organosilane was mixed with part B in a paper cup according to procedure A. Approximately 36.6 parts of part A was added and the mixture stirred. Immediately after stirring, the foam was transferred to a clean cup and allowed to foam and rise. After foaming ceased, the foam was stabilized in an oven at 200° F. for 15 minutes. The results can be found in Table II.

TABLE II

| | Results of Example 2 | | |
|---|---|---|---|
| Sample | Organosilane pbw/100 pbw polyol | % transmittance | % reduction |
| control | 0 | 12 | 0 |
| A | 0.2 | 14 | 22 |
| B | 0.5 | 14 | 0 |
| C | 1.0 | 16 | 0 |
| D | 2.0 | 29 | 100 |
| E | 3.0 | 47 | 100 |
| Blank | — | 10.5 | — |

In addition, a high resiliency flexible foam formulation was treated with 3.0 parts, based on 100 parts of polyol, of the same organosilane with the results shown as sample E. The poor showing of the samples A to C was a result of the presence of fillers in the carpet underlay formulation, which apparently absorbed the organosilane. Thus, where fillers are used as part of the foamed organic system, one must except to use slightly larger amounts of the silane. It is believed that the silane is absorbed by the filler and is tied up such that it cannot react with and become an active part of the foam.

The foam formulation, for high resiliency foam, that was used in this example was

| | | |
|---|---|---|
| 60 parts | Voranol ®-4701 | |
| 40 parts | Niax ® 34-28 polyol | |
| 3.5 parts | H$_2$O | |
| 2.0 parts | Freon ® 11 | |
| 0.1 part | Niax ® A-1 | |
| 0.8 part | A polysiloxane-polyoxyalkylene copolymer manufactured by the Dow Corning Corporation, Midland, Michigan, USA. It has a specific gravity @25° C. of 1.00; viscosity of 300 cps @25° C.; density @25° C. is 8.33 lbs./gal. and is used for high resiliency polyurethane foam | |
| 0.0075 part | Witco ® UL1 tin catalyst | |
| 1.0 part | Diethanolamine | |
| 0.55 part | Dabco ® 33 LV | |
| 39.4 parts | 80/20 toluene diisocyanate with a 105 NCO index | |

EXAMPLE 3

Standard Flexible Polyester-based Polyurethane Foam

A flexible polyester-based polyurethane foam was prepared in a paper cup in the following manner: the system consisted of part A which was toluene diisocyanate (index 105) and part B which was a mixture as follows:

| Ingredient | Parts by weight |
|---|---|
| Foamrez ® 50 | 100 |
| deionized water | 3.6 |
| Niax ® Surfactant (L-536) | 1.0 |
| Niax ® ES | 0.5 |
| Baircat ® B-16 | 0.2 |

An organosilane, $(CH_3O)_3Si(CH_2)_3N^+(CH_3)_2C_{18}H_{37}Cl^-$, was added to part B and then part A was added and the mixture was stirred. Immediately after stirring, the foaming mixture was transferred to a clean paper cup and allowed to foam and rise. When the foaming ceased, the foam was stabilized in an oven at 200° F. for 15 minutes. The results can be found on Table III.

TABLE III

Results of Example 3

| Sample | organosilane Pbw/100 parts of polyester | % transmittance | % reduction |
|---|---|---|---|
| control | 0 | 11.0 | 67.4 |
| A | 0.5 | 11.0 | 99.9 |
| B | 1.0 | 12.0 | 100 |
| C | 2.0 | 16.0 | 100 |
| D | 3.0 | 17.0 | 100 |

EXAMPLE 4

The compounds in Table IV below were each incorporated into a standard polyether-based polyurethane foam formulation at a 1.5 parts and 3.0 parts/100 parts polyol level, and tested for leachability, substantivity and antimicrobial effectiveness. No attempt was made to optimize the resulting foams. The results can be found on Table V.

TABLE IV

| Sample | Formula | Form in which it was used |
|---|---|---|
| A | $(CH_3O)_3Si(CH_2)_3N^+(CH_3)_3Cl^-$ | 50% solids in methanol |
| B | $(CH_3O)_3Si(CH_2)_3N^+(CH_3)_2C_4H_9Cl^-$ | 50% solids in methanol |
| C | $(CH_3O)_3Si(CH_2)_3N^+(CH_3)_2C_{18}H_{37}Cl^-$ | 50% solids in methanol |
| D | $(C_2H_5O)_3Si(CH_2)_3N^+(CH_3)_2C_{18}H_{37}Cl^-$ | 50% in 2B ethanol |
| E | $(CH_3O)_3Si(CH_2)_3N^+CH_3(C_{10}H_{21})_2Cl^-$ | 53% in methanol |
| F | $(CH_3O)_3Si(CH_2)_3N^+(CH_3)_2CH_2C_6H_5Cl^-$ | 70% in methanol |
| G | $(CH_3O)_3Si(CH_2)_3N^+(CH_3)_2CH_2CH_2OHCl^-$ | 50% in Dowanol ® EM |
| H | $(HO)_3Si(CH_2)_3\overset{+}{N}$(pyridinium)$Cl^-$ | 50% in water |
| I | $(CH_3O)_3Si(CH_2)_3\overset{+}{N}$(pyridinium)$Cl^-$ | 100% solids |
| J | $(CH_3O)_3Si(CH_2)_3N^+(CH_3)_2(CH_2)_3NHC(O)(CF_2)_6CF_3Cl^-$ | 100% solids |
| K | $(CH_3O)_3Si(CH_2)_3N^+(C_2H_5)_3Cl^-$ | 42% in benzylalcohol and formamide |
| L | $(CH_3O)_3Si(CH_2)_2$-(phenylene)-$CH_2N^+(C_2H_5)_3Cl^-$ | 76% in methanol |
| M | $(CH_3O)_3S(CH_2)_3N^+(CH_2CH_2)_3NCl^-$ | 48% in methanol |
| N | $(CH_3)_3N^+C_{16}H_{33}Cl^-$ + $(CH_3)_3N^+C_{18}H_{37}Cl^-$ | 100% solids |

TABLE IV-continued

| Sample | Formula | Form in which it was used |
|---|---|---|
| O | $C_{12,14,16}N^+(CH_3)_2$-C$_6$H$_5$ Cl$^-$ | 17% in water |
| P | 10,10'-oxybisphenoxarsine (OBPA) | (Thiokol, Ventron Division, Danvers, Mass., USA) |

Samples L through P are not within the scope of this invention and are shown for comparison purposes.

TABLE V

Results from Example 4

| Sample | Organosilane Pbw | % transmittance | % reduction | zone of inhibition (mm) S. aureus | zone of inhibition (mm) K. pneumoniae | Foam properties Ht. | Foam properties Airflow | Comments |
|---|---|---|---|---|---|---|---|---|
| A | 1.5 | 16.0 | 99.8 | 0 | 0 | 9-10 | 1.6 | tight foam |
| B | 1.5 | 15.0 | 43.4 | 0 | 0 | 9-8 | 5.4 | tight foam |
| B | 3.0 | 18.0 | 96.5 | 0 | 0 | | | |
| C | 1.5 | 35.0 | 100 | 0 | 0 | 9-0 | 4.5 | excellent foam |
| D | 1.5 | 31.0 | 100 | 0 | 0 | 8-12 | 6.1 | slight top blow |
| E | 1.5 | 24.0 | 100 | 0 | 0 | 9-0 | 5.5 | excellent foam |
| F | 1.5 | 15.0 | 22.6 | 0 | 0 | 9-9 | 6.0 | tight foam |
| F | 3.0 | 15.0 | 84.0 | 0 | 0 | | | |
| G | 1.5 | 22.0 | 61.3 | 0 | 0 | 9-4 | 3.2 | bottom split |
| G | 3.0 | 57.0 | 99.8 | 0 | 0 | | | |
| H | 1.5 | 45.0 | 100 | 0 | 0 | 8-11 | 5.5 | bottom split |
| I | 1.5 | 15.0 | 100 | 0 | 0 | 9-8 | 2.4 | tight foam |
| J | 1.5 | 20.0 | 97.7 | 0 | 0 | — | — | — |
| K | 1.5 | 18.0 | 50.3 | 0 | 0 | 9-4 | less than 1.0 | tight foam bottom split |
| K | 3.0 | 36.5 | 78.5 | 0 | 0 | | | |
| L | 1.5 | 27.0 | 28.7 | 0 | 0 | | | good foam |
| L | 3.0 | 23.0 | 1.6 | 0 | 0 | | | good foam |
| M | 1.5 | 16.0 | 66.6 | 0 | 0 | 9-12 | 1.6 | tight foam |
| M | 3.0 | 33.0 | 69.2 | 0 | 0 | | | bottom split tight foam |
| N | 1.5 | 52.0 | 100 | 2 | 0 | 8-12 | 7.9 | center blow out |
| O | 1.5 | 63.0 | 100 | 5 | 0 | 8-0 | — | shrink |
| P | — | — | — | 11 | 4 | | | |
| Blank | | 10.5 | — | — | — | | | |

EXAMPLE 5

A polyurethane foam filter

Two Buchner filter funnels were set up and the inside bottom of each funnel was covered with a #1 Whatman filter paper which had been sterilized. Standard flexible polyurethane foam plugs, approximately the diameter of the funnel and about 7 cm thick were cut from foam stock which contained 3.0 parts of $(CH_3O)_3$-$Si(CH_2)_3N(CH_3)_2C_{18}H_{37}Cl^-$ per one hundred parts of polyol.

A titer of organisms was prepared from K. pneumoniae in 600 ml phosphate buffer. This titer was passed through the Buchner funnel/polyurethane filter system into a sterile dish. The solution was then diluted and pour plated and incubated.

Using this system, it was determined that the treated foam caused a 100% kill of the microorganism on one pass while a similar, non-treated foam caused only a 15% reduction in the number of microorganisms.

It should be noted that the cationic silane-containing foam released quite readily from the Buchner funnel while the standard foam could not be removed at all. Thus, the cationic silanes of this invention are also release agents for the foams they are prepared with.

EXAMPLE 6

Standard Rigid Polyurethane Foam

A rigid polyurethane foam was prepared according to the standard procedure "A" set forth above and using the following premix formulation:

| | |
|---|---|
| Pluracol ® 364 | 90 parts |
| Fyrol ® 6 | 10 parts |
| deionized water | 0.5 parts |
| Niax ® | 40 parts |
| Blowing Agent 11B | |
| Polycat ® 8 | 0.5 parts |

Fifty grams of the above premix were placed in a 1 quart paper cup and there was added thereto 0.4 gm of a silicone surfactant which is a polysiloxane polyoxyethylene copolymer surfactant (62.5% ethylene oxide; 27.4% siloxane) having a specific gravity of 1.068 @ 25° C.; a viscosity of 425 cps @ 25° C. and a density of 8.91 lbs./gal. It is a rigid polyurethane foam surfactant. Variable gms of silane as a 42 weight percent aqueous-alcoholic solution and 46.5 gms of Mondur ® M.R. were added. This was mixed for 10 seconds and allowed to rise. The organosilane used herein in the amounts shown in Table VII was $(CH_3O)_3$-$Si(CH_2)_3N^+(CH_3)_2C_{18}H_{37}Cl^-$ (silane). The results are shown on Table VII.

TABLE VII

Results from Example 6

| sample | Organosilane pbw/100 parts polyol | % transmittance | % reduction | comments |
| --- | --- | --- | --- | --- |
| control | 0 | 11.3 | 54.2 | acceptable |
| A | 2.8 | 11.8 | 44.9 | acceptable |
| B | 28 | 10.8 | 94.5 | acceptable |
| C | 56 | 11.8 | 99.9 | acceptable |
| D | 112 | 41.0 | 100 | Foam Collapsed |
| Blank | | 11.0 | 9.4 | — |

EXAMPLE 7

Preparation of a Vinyl Foam

A vinyl foam was prepared using the following formulation:

| | |
| --- | --- |
| 100 parts | Dioctylphthalate |
| 85 parts | Polyvinylchloride resin (Bordon ® 411) |
| 4 parts | Dow Corning ® 1250 Surfactant |
| vary | $(CH_3O)_3Si(CH_2)_3N^+(CH_3)_2C_{18}H_{37}Cl^-$ (organosilane) |

The resulting foam was very dense and difficult to wet out with water but the bromophenol blue test indicated that the incorporation of the organosilane was very effective. The results of the testing can be found on Table VIII.

TABLE VIII

Results from Example 7

| Sample | organosilane (pbw) | % transmittance | % reduction |
| --- | --- | --- | --- |
| control | 0 | 11.0 | 2.5 |
| A | 2 | 10.8 | 8.5 |
| B | 5 | 11.0 | 88.2 |
| Blank | | 10.8 | — |

EXAMPLE 8

An attempt was made to determine the optimum level of antimicrobial agent in a foam formulation. The antimicrobial agent used was $(CH_3O)_3Si(CH_2)_3N^{\oplus}(CH_3)_2C_{18}H_{37}Cl^-$. The foam formulation was a standard flexible polyurethane foam formulation and can be found in the specification as standard procedure "A". After foaming, the foams were tested for biological activity and foam physical properties, without regard to optimization of foam properties. The results can be found in Table IX. The amount of the antimicrobial agent was based on 100 parts of polyol.

TABLE IX

Results from Example 8

| Sample | amount silane in parts | % transmittance | % reduction | Foam Formed |
| --- | --- | --- | --- | --- |
| A | 0 | 12 | 0 | yes |
| B | .05 | 12 | 1.5 | yes |
| C | .20 | 12 | 0 | yes |
| D | .50 | 13 | 6.3 | yes |
| E | .80 | 14 | 1.5 | yes |
| F | 1 | 17 | 7.9 | yes |
| G | 5 | 99 | 100 | yes |
| H | 10 | 63 | 100 | yes |
| I | 20 | — | — | no |
| J | 40 | — | — | no |
| K | 80 | — | — | no |
| Blank | — | 11.5 | — | — |

EXAMPLE 9

Leaching studies were performed on an antimicrobial agent of this invention and a comparison was made against a commercial antimicrobial agent, namely, 10,10'-oxybisphenoxarsine (OBPA) (Thiokol, Ventron Division, Danvers, Mass., USA).

The OBPA samples were prepared in the following manner:

Ten, 1"×1"×½" squares of polyurethane foam were cut from foamed slabs in which OBPA was used. The foam was manufactured by North Carolina Foam Industries, Mount Airy, N.C. The squares weighed about 0.185 grams each. The squares were placed in 8 oz. French square glass bottles in sets of two and 150 ml of deionized water was added at room temperature. The bottles were placed on a Burrell wrist action shaker and shook for 15 minutes on the highest agitation. The samples from one bottle were removed from the water and squeezed by hand to remove excess water and then dried in an air circulating oven for 15 minutes at 50° C. The remainder of the botles were handled by pouring off the water, squeezing the samples to remove excess water, returning the samples to the bottle and adding a fresh batch of 150 ml of deionized water. Thus there was obtained a series of foam samples that had been washed a varying number of times. These samples, after drying, were tested for zone of inhibition on Brain Heart Infusion (Difco Labs, Detroit, Mich., U.S.A.) media plates and the ability to reduce the number of organisms in a solution.

Samples of foam prepared from a flexible polyurethane foam formulation containing 3 parts of $(CH_3O)_3Si(CH_2)_3N^+(CH_3)_2C_{18}H_{37}Cl^-$ (silane) were handled the same way as the OBPA samples except that the samples were cut large enough to equal 1.5 gms. This resulted in a liquor to material ratio of 10:1 when 150 ml of deionized water was used (approximately 8 times the amount of foam as was used in the OBPA foam samples). These samples were tested the same as the OBPA samples and they can be compared in Table X, below.

TABLE X

Results of Example 9

| Sample | Agent | Washes | % transmittance | % reduction | zone of inhibition/mm S. aureus | zone of inhibition/mm K. pneumoniae |
| --- | --- | --- | --- | --- | --- | --- |
| A | silane | 0 | 35.0 | 100 | 0 | 0 |
| B | silane | 1 | 22.0 | 100 | 0 | 0 |
| C | silane | 4 | 23.1 | 100 | 0 | 0 |
| D | silane | 7 | 17.0 | 99.9 | 0 | 0 |
| E | silane | 10 | 17.5 | 99.9 | 0 | 0 |
| F | silane | 13 | 16.9 | 86.3 | 0 | 0 |
| G | OBPA | 0 | — | 0 | 5 | 2 |
| H | OBPA | 1 | — | 0 | 3 | 0 |
| I | OBPA | 4 | — | 0 | 0 | 0 |
| J | OBPA | 7 | — | 0 | 0 | 0 |
| K | OBPA | 10 | — | 0 | 0 | 0 |
| L | OBPA | 13 | — | 0 | 0 | 0 |

It can be observed from the results that the OBPA is subject to fast leaching from the foam substrate as can be concluded from the initial zone of inhibition and the lack of a zone after 1 wash or more with a consequent inability to reduce the number of organisms in the test specimen whereas the sample of this invention with silane showed little or no leaching tendencies and maintained its ability to reduce the number of viable organisms in the test sample, even after 13 washings.

EXAMPLE 10

A silane of this invention was used in a standard flexible polyurethane foam formulation as in example 1, using Standard Procedure "A" and the amount of amine catalyst and tin catalyst were adjusted in order to show that the silane can substitute for part of each such catalyst in a foam system. The use of lesser amounts of both of such catalysts leads to the production of economical foams without sacrificing essential foam physical properties. The silane used was $(CH_3O)_3$-$Si(CH_2)_3N^+(CH_3)_2C_{18}H_{37}Cl^-$ (silane). The results can be found in Table XI below.

TABLE XI

Results from Example 10

| Sample | parts silane | parts amine | parts tin catalyst | Foam Height/in. | Air Flow (cfm) |
|---|---|---|---|---|---|
| control | 0 | 0.1 | 0.4 | 9 | 7.2 |
| A | 1.0 | 0.1 | 0 | 9 | 5.9 |
| B | 2.0 | 0.1 | 0 | 9 | 5.8 |
| C | 1.0 | .05 | 0 | 9 | 6.5 |
| D | 2.0 | .05 | 0 | 9 | 4.4 |
| E | 1.0 | 0 | 0 | 9 (bottom split) | 2.0 |
| F | 2.0 | 0 | 0 | 9 (bottom split) | 1.6 |
| G | 1.0 | 0.1 | .35 | 9 | 6.9 |
| H | 2.0 | 0.1 | .35 | 9 | 6.9 |
| I | 1.0 | .05 | .35 | 9 | 7.5 |
| J | 2.0 | .05 | .35 | 9 | 7.4 |
| K | 1.0 | .05 | .30 | 8–14 | 7.3 |
| L | 2.0 | .05 | .30 | 8–14 | 7.4 |

Thus it can be observed that the tin catalyst in this example can be decreased by 15% and the amine catalyst can be reduced by 50% without sacrificing essential foam physical properties.

EXAMPLE 11

Two, 4½ inch diameter, glass Buchner funnels were sterilized and filled with standard, flexible polyurethane foam plugs, after placing a Whatman filter paper in the bottom of the flask to cover the holes. The foam was prepared in a manner similar to example 1 except that the tin catalyst was reduced in the formulation to 0.35 parts in order to increase the size of the foam cells slightly. There was used 3.0 parts by weight of $(CH_3O)_3Si(CH_2)_3N^+(CH_3)_2C_{18}H_{37}Cl^-$ based on 100 parts of polyol. The resulting foam was stabilized at 200° F. for 15 minutes in an air circulating oven.

*Klebsiella pneumoniae* (ATCC 4352) was grown for 18 hours in nutrient broth. An optical density O.D. 22 of the culture was prepared using a Spectronic (Bausch and Lomb) spectrophotometer. A 1:100 dilution of the O.D. culture was made in phosphate buffer. Two mls of the 1:100 dilution were transferred to a flask containing 800 mls of sterile buffer. Two flasks of the above culture were thus prepared; one to be filtered through the control foam and one to be filtered through the treated foam. Initial bacterial counts were made by standard pour plate techniques from each flask. The bacterial suspensions were then pumped, by the use of a miniparastaltic pump, through the foam filters in the Buchner funnels, in a continuous loop for 60 minutes. The suspensions were checked for colonly units. The treated foam reduced the number of viable colonies to zero. The results are shown on Table XII.

TABLE XII

Results from Example 11

| | Number of Viable Colony Forming Units | |
|---|---|---|
| Sample | zero time | 60 minutes |
| control | 4450 | 26700 |
| treated | 5650 | 0 |

EXAMPLE 12

The test of Example 11 was repeated except the the final dilution was in nutrient broth rather than the buffer solution with the idea in mind to fortify the organisms over the time period as they were being tested. The results are shown on Table XIII.

TABLE XIII

Results from Example 12

| | Number of Viable Colony Forming Units | |
|---|---|---|
| Sample | zero time | 45 minutes |
| control | 4000 | 121,000 |
| treated | 5050 | 12,300 |

EXAMPLE 13

A test was performed to determine the ability of a foam from this invention to kill a wide variety of organisms. The organisms were clinical isolates, isolated from urinary tract infections and were
1. *Escherichia coli*
2. *Pseudomonas fluorescens*
3. *Proteus mirabilis*
4. *Staphlococcus aureus*
5. Enterococcus The test was carried out by subjecting each of the above organisms to standard test "C". The foam samples were standard polyurethane foam samples that were prepared using 3 parts of $(CH_3O)_3$-$Si(CH_2)_3N^+(CH_3)_2C_{18}H_{37}Cl^-$ per 100 parts of polyol. The results can be found on Table XIV.

TABLE XIV

Results from Example 13

| organism | sample | % Reduction |
|---|---|---|
| 1 | control | 5.4 |
| 1 | treated | 100 |
| 2 | control | 20.1 |
| 2 | treated | 100 |
| 3 | control | 0 |
| 3 | treated | 89.2 |
| 4 | control | 0 |
| 4 | treated | 99.9 |
| 5 | control | 0 |
| 5 | treated | 100 |

EXAMPLE 14

This experiment was carried out to determine if microorganisms would adapt to and survive in the presence of an antimicrobial foam of this invention.

A foam sample was prepared via the standard procedure "A" using 3 parts of $(CH_3O)_3$-$Si(CH_2)_3N^+(CH_3)_2C_{18}H_{37}Cl^-$ per 100 parts of polyol. A comparison sample of polyurethane foam containing OBPA was obtained from North Carolina Foam Industries, Inc., Mount Airy, N.C., U.S.A.

Standard test "C" was used to determine antimicrobial activity and zone of inhibition testing was done to determine if and when adaptability of the microorganism to the treatment was obtained. It should be noted that the instant invention antimicrobial agents are essentially non-leachable and therefore there is no zone of inhibition to be tested. The testing of zone of inhibition consisted of doing a number of consecutive zone of inhibition tests as was set forth in Example 11 using two different organisms. The organism for each new consecutive test was taken from the edge of the zone of inhibition from the previous zone of inhibition test. Five zone tests were done.

For the standard test "C", each sample was exposed to the organism in solution 5 times, each time being interrupted and standard test "C" was carried out. Caution was taken with the silane treated sample so that not all the microorganisms were killed in order to preserve a few to carry to the next test. The results are shown on Table XV.

TABLE XV

| | Results from Example 14 | | |
|---|---|---|---|
| Sample | Consecutive Test Number | Zone of Inhibition | | % Reduction |
| | | Staph. aureus | Kleb. pneu. | |
| OBPA | 1 | 2 | 6 | — |
| Invention | 1 | 0 | 0 | 100 |
| OBPA | 2 | 2 | 5 | — |
| Invention | 2 | 0 | 0 | 100 |
| OBPA | 3 | 1 | 4 | — |
| Invention | 3 | 0 | 0 | 99.9 |
| OBPA | 4 | 1 | 2 | — |
| Invention | 4 | 0 | 0 | 100 |
| OBPA | 5 | 0 | 0 | — |
| Invention | 5 | 0 | 0 | 100 |

It is quite clear that adaptation was taking place with the OBPA sample, while the silane treated sample showed no decrease in its ability to kill the organisms following repeated exposures.

That which is claimed is:

1. A process for preparing an antimicrobially active non-filled stable foam which comprises (I) contacting and intimately mixing, prior to foaming, a foamable organic system and an organosilane having the general formula selected from the group consisting of

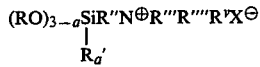

and

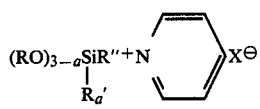

wherein, in each formula,
   R is an alkyl radical of 1 to 4 carbon atoms or hydrogen;
   a has a value of 0, 1 or 2;
   R' is a methyl or ethyl radical;
   R" is an alkylene group of 1 to 4 carbon atoms;
   R''', R'''' and R$^v$ are each independently selected from a group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$, wherein x has a value of from 2 to 10 and R$^{vi}$ is a perfluoroalkyl radical having from 1 to 12 carbon atoms;
   X is chloride, bromide, fluoride, iodide, acetate or tosylate;, and (II) foaming the mixture from (I), and
   (III) allowing the foamable organic system to stabilize, whereby an antimicrobially active stable foam is obtained.

2. A process as claimed in claim 1 wherein the foamable organic system is a polyurethane.

3. A process as claimed in claim 2 wherein the polyurethane is polyether based.

4. A process as claimed in claim 2 wherein the polyurethane is polyester based.

5. A process as claimed in claim 1 wherein the foamable organic system is vinyl based.

6. A process as claimed in claim 1 wherein the foamable organic system is polystyrene based.

7. A process as claimed in claim 1 wherein the foamable organic system is nylon based.

8. A process as claimed in claim 1 wherein the organosilane has the formula

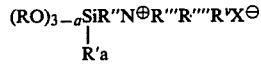

wherein R is an alkyl radical of 1 to 4 carbon atoms or hydrogen; a has a value of 0, 1 or 2; R' is a methyl or ethyl radical; R" is an alkylene group of 1 to 4 carbon atoms; R''', R'''' and R$^v$ are each independently selected from a group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$, wherein x has a value of from 2 to 10 and R$^{vi}$ is a perfluoroalkyl radical having from 1 to 12 carbon atoms; X is chloride, bromide, fluoride, iodide, acetate or tosylate.

9. A process as claimed in claim 8 wherein a is zero, R is methyl, R" is propylene, R''', R'''' and R$^v$ are each methyl and X is chloride.

10. A process as claimed in claim 8 wherein a is zero, R is methyl, R" is propylene, R''' and R'''' are methyl, R$^v$ is butyl and X is chloride.

11. A process as claimed in claim 8 wherein a is zero, R is methyl, R" is propylene, R''', R'''' and R$^v$ are each ethyl and X is chloride.

12. A process as claimed in claim 8 wherein a is zero, R is methyl, R" is propylene, R''' and R'''' are each methyl, R$^v$ is octadecyl and X is chloride.

13. A process as claimed in claim 8 wherein a is zero, R is methyl, R" is propylene, R''' is methyl, R'''' and R$^v$ are each decyl and X is chloride.

14. A process as claimed in claim 8 wherein a is zero, R is methyl, R" is propylene, R''' and R'''' are methyl, R$^v$ is —CH$_2$C$_6$H$_5$ and X is chloride.

15. A process as claimed in claim 8 wherein a is zero, R is methyl, R" is propylene, R''' and R'''' are methyl, R$^v$ is —CH$_2$CH$_2$OH and X is chloride.

16. A process as claimed in claim 8 wherein a is zero, R is ethyl, R" is propylene, R''' and R'''' are methyl, R$^v$ is octadecyl and X is chloride.

17. A process as claimed in claim 8 wherein a is zero, R is ethyl, R" is propylene, R''' is methyl, R'''' and R$^v$ are decyl and X is chloride.

18. A process as claimed in claim 8 wherein a is one, R is methyl, R' is methyl, R" is propylene, R''' and R'''' are methyl, R$^v$ is octadecyl and X is chloride.

19. A process as claimed in claim 8 wherein a is one, R is ethyl, R' is methyl, R" is propylene, R''' and R'''' are methyl, R$^v$ is octadecyl and X is chloride.

20. A process as claimed in claim 8 wherein a is one, R is methyl, R' is methyl, R" is propylene, R'" is methyl, R"" and R$^v$ are decyl and X is chloride.

21. A process as claimed in claim 8 wherein a is one, R is ethyl, R' is methyl, R" is propylene, R'" is methyl, R"" and R$^v$ are decyl and X is chloride.

22. A process as claimed in claim 8 wherein a is two, R is methyl, R' is methyl, R" is propylene, R'" and R"" are methyl, R$^v$ is octadecyl and X is chloride.

23. A process as claimed in claim 8 wherein a is two, R is ethyl, R' is methyl, R" is propylene, R'" and R"" are methyl, R$^v$ is octadecyl and X is chloride.

24. A process as claimed in claim 8 wherein a is two, R is ethyl, R' is methyl, R" is propylene, R'" is methyl, R"" and R$^v$ are decyl and X is chloride.

25. A process as claimed in claim 8 wherein a is two, R is ethyl, R' is methyl, R" is propylene, R'" is methyl, R"" and R$^v$ are decyl and X is chloride.

26. A process as claimed in claim 8 wherein a is zero, R is methyl, R" is propylene, R'" and R"" are methyl, R$^v$ is $-(CH_2)_xNHC(O)R^{vi}$ and X is chloride.

27. A process as claimed in claim 26 wherein x has a value of 2 and R$^{vi}$ is $-(CF_2)_6CF_3$.

28. A process as claimed in claim 26 wherein x has a value of 3 and R$^{vi}$ is $-(CF_2)_6CF_3$.

29. A process as claimed in claim 1 wherein the organosilane has the formula

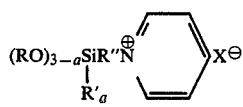

wherein R is an alkyl radical of 1 to 4 carbon atoms or hydrogen; a has a value of 0, 1 or 2; R' is a methyl or ethyl radical; R" is an alkylene of 1 to 4 carbon atoms; X is chloride, bromide, fluoride, iodide, acetate or tosylate.

30. A process as claimed in claim 29 wherein a is zero, R is methyl, R" is propylene, X is chloride and bonded to a pyridinyl nitrogen atom.

31. A process as claimed in claim 29 wherein a is zero, R is ethyl, R" is propylene, X is chloride and bonded to a pyridinyl nitrogen atom.

32. A process as claimed in claim 29 wherein a is zero, R is hydrogen, R" is propylene, X is chloride and bonded to a pyridinyl nitrogen atom.

33. A stable foam prepared by the process of claim 1.
34. A stable foam prepared by the process of claim 2.
35. A stable foam prepared by the process of claim 3.
36. A stable foam prepared by the process of claim 4.
37. A stable foam prepared by the process of claim 5.
38. A stable foam prepared by the process of claim 6.
39. An article when manufactured from the foam of claim 33.
40. An article when manufactured from the foam of claim 34.
41. An article when manufactured from the foam of claim 35.
42. An article when manufactured from the foam of claim 36.
43. An article when manufactured from the foam of claim 37.
44. An article when manufactured from the foam of claim 38.
45. An article as claim in claim 39 which is a backing.
46. An article as claimed in claim 45 which is carpet backing.
47. An article as claimed in claim 45 which is a curtain backing.
48. An article as claimed in claim 45 which is a wall rug backing.
49. An article as claimed in claim 45 which is a wall hanging backing.
50. An article as claimed in claim 39 which is a mattress.
51. An article as claimed in claim 39 which is a cushion.
52. An article as claimed in claim 51 which is an auto cushion.
53. An article as claimed in claim 51 which is a furniture cushion.
54. An article as claimed in claim 39 which is a pillow.
55. An article as claimed in claim 39 which is a lapidus pad.
56. An article as claimed in claim 39 which is a decubitus pad.
57. An article as claimed in claim 39 which is an air filter.
58. An article as claimed in claim 57 which is a clean room air filter.
59. An article as claimed in claim 57 which is an air conditioning filter.
60. An article as claimed in claim 59 which is an industrial air conditioning filter.
61. An article as claimed in claim 59 which is a non-industrial air conditioning filter.
62. An article as claimed in claim 61 which is an automotive air filter.
63. An article as claimed in claim 61 which is a residential air filter.
64. An article as claimed in claim 39 which is a filter for a liquid.
65. An article as claimed in claim 64 which is a filter for blood.
66. An article as claimed in claim 64 which is a filter for blood products.
67. An article as claimed in claim 64 which is a filter for fermented spirits.
68. An article as claimed in claim 67 wherein the fermented spirit is wine.
69. An article as claimed in claim 67 wherein the fermented spirit is beer.
70. An article as claimed in claim 64 which is a filter for water.
71. An article as claimed in claim 70 which is a swimming pool filter.
72. An article as claimed in claim 70 which is a coolant system filter.
73. An article as claimed in claim 70 which is a waste water filter.
74. An article as claimed in claim 70 which is a potable water filter.
75. An article as claimed in claim 70 which is an aquarium filter.
76. An article as claimed in claim 64 which is a filter for milk.
77. An article as claimed in claim 39 which is a sponge.
78. An article as claimed in claim 39 which is a humidifier belt.
79. An article as claimed in claim 39 which is used for thermal insulation.

80. A process as claimed in claim 1 wherein the foamable organic system containing the silane is sprayed in place.

81. A process as claimed in claim 80 wherein the foamable organic system containing the silane is applied from an aerosol package.

82. An article as claimed in claim 39 which is a filter for a gas.

83. An article as claimed in claim 82 wherein the gas is air.

84. An article as claimed in claim 82 wherein the gas is oxygen.

85. An article as claimed in claim 82 wherein the gas is nitrogen.

86. An article as claimed in claim 82 wherein the gas is carbon dioxide.

87. A method of sterilizing a liquid which method comprises passing the liquid through a foam filter, said foam filter being prepared by the process of claim 1.

88. A method as claimed in claim 87 wherein the foam is polyurethane and the liquid is water.

89. A method as claimed in claim 87 wherein the foam is polyurethane and the liquid is blood.

90. A method as claimed in claim 87 wherein the foam is polyurethane and the liquid is a blood product.

91. A method as claimed in claim 87 wherein the foam is polyurethane and the liquid is a fermented spirit.

92. A method as claimed in claim 87 wherein the foam is polyurethane and the liquid is milk.

93. A method of sterilizing a gas which method comprises passing the gas through a foam, said foam being prepared by the process of claim 1.

94. A method as claimed in claim 93 wherein the gas is air.

95. A method as claimed in claim 93 wherein the gas is oxygen.

96. A method as claimed in claim 93 wherein the gas is nitrogen.

97. A method as claimed in claim 93 wherein the gas is carbon dioxide.

98. A method as claimed in claim 93 wherein there is a mixture of gases.

99. A process for preparing an antimicrobially active non-siliceous filled stable foam which comprises (I) contacting and intimately mixing, prior to foaming, a foamable organic system and an organosilane having the general formula selected from the group consisting of

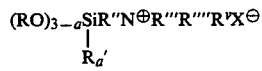

and

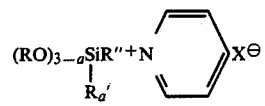

wherein, in each formula,

R is an alkyl radical of 1 to 4 carbon atoms or hydrogen;

a has a value of 0, 1 or 2;

R' is a methyl or ethyl radical;

R'' is an alkylene group of 1 to 4 carbon atoms;

R''', R'''' and $R^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms;

X is chloride, bromide, fluoride, iodide, acetate or tosylate;, and (II) foaming the mixture from (I), and (III) allowing the foamable organic system to stabilize, whereby an antimicrobially active stable foam is obtained.

100. A process as claimed in claim 99 wherein the organosilane has the formula

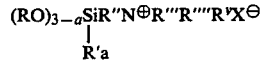

wherein R is an alkyl radical of 1 to 4 carbon atoms or hydrogen; a has a value of 0, 1 or 2; R' is a methyl or ethyl radical; R'' is an alkylene group of 1 to 4 carbon atoms; R''', R'''' and $R^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms; X is chloride, bromide, fluoride, iodide, acetate or tosylate.

101. A process as claimed in claim 100 wherein a is zero, R is methyl, R'' is propylene, R''' and R'''' are each methyl, $R^v$ is octadecyl and X is chloride.

102. A process as claimed in claim 100 wherein a is zero, R is methyl, R'' is propylene, R''' is methyl, R'''' and $R^v$ are each decyl and X is chloride.

103. A stable foam prepared by the process of claim 99.

104. An article when manufactured from the foam of claim 103.

105. An article as claimed in claim 104 which is a backing.

106. An article as claimed in claim 105 which is carpet backing.

107. An article as claimed in claim 105 which is a curtain backing.

108. A process as claimed in claim 99 wherein the foamable organic system containing the silane is sprayed in place.

* * * * *